United States Patent [19]

Bartek et al.

[11] 4,292,455
[45] Sep. 29, 1981

[54] MULTI-STAGE DEHYDROGENATION PROCESS FOR PREPARING INDENE

[75] Inventors: Joseph P. Bartek, University Heights; Rimoydas L. Cepulis, Euclid; Robert K. Grasselli, Chagrin Falls, all of Ohio

[73] Assignee: The Standard Oil Co., Cleveland, Ohio

[21] Appl. No.: 108,328

[22] Filed: Dec. 28, 1979

[51] Int. Cl.³ .......................... C07C 5/42; C07C 5/367; C07C 4/12; C07C 5/48
[52] U.S. Cl. .................................... 585/320; 585/361; 585/400; 585/410; 585/415; 585/422; 585/430; 585/431; 585/433; 585/443; 585/444
[58] Field of Search ............... 585/320, 361, 400, 410, 585/415, 422, 430, 431, 433, 443, 444

[56] References Cited

U.S. PATENT DOCUMENTS

| | | | |
|---|---|---|---|
| 2,519,577 | 8/1950 | Ipatieff | 585/410 |
| 2,763,701 | 9/1956 | Hoffmann et al. | 585/400 |
| 2,984,692 | 5/1961 | Lederle | 585/400 |
| 3,183,249 | 5/1965 | Weise | 585/360 |
| 3,502,736 | 3/1970 | Sato et al. | 585/443 |
| 3,728,406 | 4/1973 | Vrinssen et al. | 585/360 |
| 3,853,291 | 12/1974 | Feins | 208/216 PP |
| 3,887,631 | 6/1975 | Yaffe | 585/445 |
| 3,925,498 | 12/1975 | Stadig | 585/625 |
| 3,933,932 | 1/1976 | Vrieland | 585/444 |
| 4,143,082 | 3/1979 | Bartek et al. | 585/437 |

OTHER PUBLICATIONS

Chem. Abs., 55, 16506b.
Chem. Abs., 74, 76220.
Chem. Abs., 75, 63494.

Primary Examiner—Curtis R. Davis
Attorney, Agent, or Firm—J. E. Miller, Jr.; H. D. Knudsen; Larry W. Evans

[57] ABSTRACT

A multi-stage dehydrogenation process for preparing indene and substituted indenes from indene precursors more saturated than indene is described. The process comprises the steps of (a) contacting said indene precursor in a first dehydrogenation zone with a dehydrogenation catalyst at an elevated temperature to form an intermediate product, (b) advancing the product of the first dehydrogenation zone to a second dehydrogenation zone, (c) contacting said product in the second dehydrogenation zone with a second dehydrogenation catalyst at an elevated temperature, and (d) recovering indene or a substituted indene from said second zone.

The process of the invention results in yields of indene which are enhanced when compared to single stage, essentially isothermal processes using a single catalyst.

16 Claims, 1 Drawing Figure

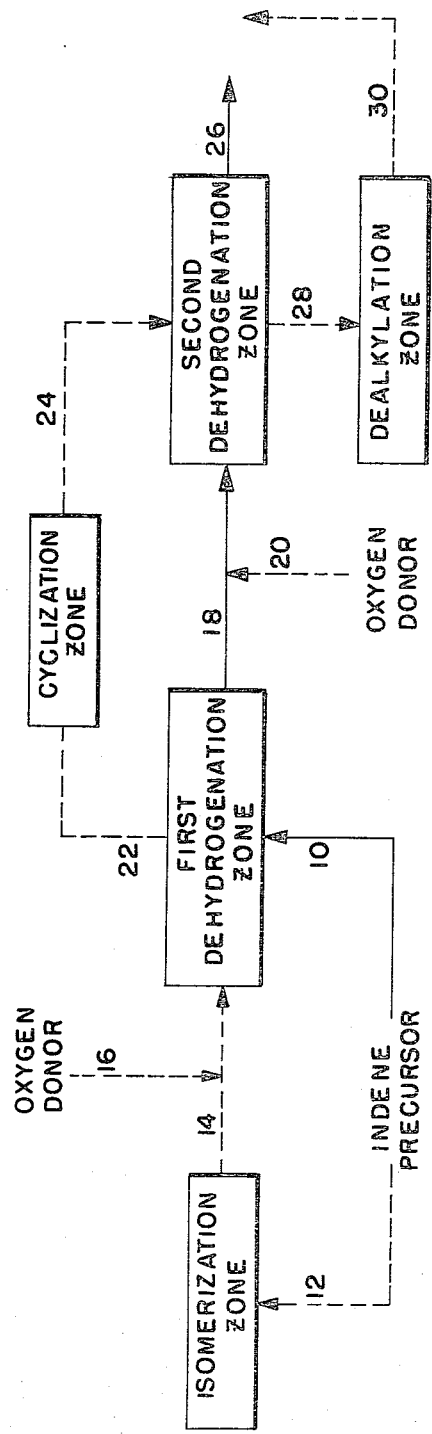

MULTI-STAGE DEHYDROGENATION PROCESS FOR PREPARING INDENE

BACKGROUND OF THE INVENTION

This invention relates to an improved dehydrogenation process for producing indene and substituted indenes, and more particularly, to a multi-stage dehydrogenation process.

Indene is present in low concentrations (e.g. 12–16%) in ethylene or gas oil cracking coproducts, but is has been difficult to recover the indene in satisfactory yields and purity from these low concentration sources. Indene is a desirable raw material for preparing superior heat-resistant polymers.

The invention of this application is directed particularly to the preparation of indene and substituted indene from tetrahydroindene and substituted tetrahydroindene. Tetrahydroindene along with other products are formed in Diels-Alder reactions of butadiene with cyclopentadiene or its dimer, dicyclopentadiene. Substituted tetrahydroindenes are obtained when a substituted butadiene is used in the reaction. A considerable amount of research has been conducted and published on this reaction, and various suggestions have been made for optimizing the production of the various coproducts such as vinyl cyclohexene and vinyl norbornene.

The dehydrogenation of indene precursors such as tetrahydroindene into indene has been described in the art and generally is conducted in the presence of dehydrogenation promoting catalysts. In U.S. Pat. No. 4,143,082, the dehydrogenation of indene precursors into indene is accomplished by contacting the indene precursor in the presence of an oxygen donor with a phosphate catalyst at elevated temperature. These catalsyts, described more fully in the patent, are salts of one of the phosphoric acids. Other types of dehydrogenation catalyst have been described in the literature, and such compounds include the metal oxides, metal salts such as the halides, phosphates, sulfates, molybdates, tungstates, etc. Generally, these catalysts are characterized as compounds containing a metal having a polyoxidation state, that is, a metal having at least two oxidation states in addition to the zero state. Examples of useful polyoxidation state metals include Ti,V,Cr,Mn,Co,Ni,Cu,Nb,Mo,Ru, etc.

In addition to the use of polyoxidative state metals, oxidation catalysts also may be combined with one or more monooxidation state metals which act as promoters, initiators, stabilizers and the like. The single oxidation state metal or metal compounds include the alkali metals, and polyvalent metals such as magnesium, aluminum, calcium, scandium, zinc, etc. The use of cobalt and molybdenum oxides promoted with potassium oxide in dehydrogenating indane to indene is reported in Czech U.S. Pat. No. 135,251. The catalyst bed contained 3% CoO, 10% $MoO_3$ and 0.3% $K_2O$. A review of the various catalysts useful in oxidative dehydrogenation of organic compounds is found in U.S. Pat. No. 3,925,498. U.S. Pat. No. 3,887,631 describes the oxidative dehydrogenation of hydrocarbons such as butene and ethylhexane by use of a catalyst consisting essentially of the oxides of molybdenum, cobalt and boron.

U.S. Pat. No. 3,925,498 describes an oxidative dehydrogenation procedure which utilizes a multiple bed reactor and wherein incremental amounts of oxygen are added to the organic compounds to be dehydrogenated as the organic compounds pass through the reactor. The mixing of the oxygen and the organic compounds occurs in those areas where the catalyst is not present.

SUMMARY OF THE INVENTION

It now has been found that the highly desirable conversion of indene precursors more saturated than indene, and particularly, tetrahydroindene and substituted tetrahydroindene to indene and indene derivatives can be accomplished at desirable selectivity and yield by a multi-stage dehydrogenation process. More particularly, the process of the invention comprises the steps of (a) contacting said indene precursor in a first dehydrogenation zone with a dehydrogenation catalyst at an elevated temperature to form an intermediate product, (b) advancing the product of the first dehydrogenation zone to a second dehydrogenation zone, (c) contacting said product in the second dehydrogenation zone with a second dehydrogenation catalyst at an elevated temperature, and (d) recovering indene or a substituted indene from said second zone.

An oxygen source can be added to the first or the second dehydrogenation zones to to both zones in a preferred method.

BRIEF DESCRIPTION OF THE DRAWING

The FIGURE is a flow diagram showing one modification of the operation of the process of this invention.

DESCRIPTION OF THE PREFERRED EMBODIMENT

In accordance with the present invention, indene and substituted indenes are produced from indene precursors by a multi-stage catalytic dehydrogenation process.

The indene precursors may be any compound more saturated than indene which can be dehydrogenated or oxydehydrogenated to indene or a substituted indene. The precursors may be alkyl or alkenyl benzenes containing at least 3 carbon atoms such as n-propyl benzene or cumene, or substituted or unsubstituted bicyclic indene precursors more saturated than indene. The substituted bicyclic compounds can contain one or more alkyl or alkenyl groups having from one to four carbon atoms or can contain phyenl groups attached to one or both rings of the bicyclic compound. The substituted indenes obtained from these precursors normally have the corresponding alkyl, alkenyl or phenyl groups attached although there may be fewer groups or fewer carbon atoms in the groups.

Examples of bicyclic precursors which may be oxydehydrogenated in accordance with the invention include indane, alkyl (especially methyl) indanes in which the alkyl groups have from 1 to 4 carbon atoms, tetrahydroindene (especially the bicyclo(4.3.0) nona-3,7-diene isomer), alkyl tetrahydroindenes in which the alkyl groups have from 1 to 4 carbon atoms, hexahydroindene, hexahydroindane and vinyl norborene (5-vinyl bicyclo- (2.2.1)-2-heptene).

The multi-stage process of the invention is illustrated in the drawing. The indene precursor which is to be treated in accordance with the process of the invention generally is advanced to a first dehydrogenation zone as indicated by arrow 10. Certain precursors, like vinyl norbornene, require isomerization to other precursors such as tetrahydroindene before dehydrogenation to indene and other indene precursors can occur efficiently in the first dehydrogenation zone. Accordingly, when the indene precursor is a material requiring isomerization, the precursors advance to the isomerization zone as indicated by arrow 12 where the material is contacted with an isomerization catalyst and isomerized to a material more easily dehydrogenated to indene. Acid isomerization catalysts such as boron phosphate, $SiO_2$–$Al_2O_3$, zeolites, etc., are useful catalysts in the isomerization zone. Alternatively, though not preferred, the isomerization catalysts can be included in the first dehydrogenatin zone with the dehydrogenation catalyst. The material which is isomerized in the isomerization zone is advanced to the first dehydrogenation zone as indicated by arrow 14. In the first dehydrogenation zone, the indene precursor is contacted with a dehydrogenation catalyst at an elevated temperature to form an intermediate product. Generally, the conditions within the first dehydrogenation zone are less severe than those within the second dehydrogenation zone. These conditions include the temperatures within the dehydrogenation zones and the catalysts selected for the dehydrogenation.

The various dehydrogenation catalysts which have been described in the prior art can be utilized in the multi-stage process of the invention. The temperature within the first dehydrogenation zone generally is at least 100° C. In one emobidment of the invention shown in the drawing, an oxygen donor can be advanced to the first dehydrogenation zone as indicated by broken arrow 16, and the indene precursor is contacted with the dehydrogenation catalyst in the presence of the oxygen donor. In this instance, oxydehydrogenation of the indene precursor occurs in the first dehydrogenation zone. The product of the first dehydrogenation zone will comprise some indene and a variety of intermediate indene precursors at various stages of dehydrogenation including, for example, indane. The product of the first dehydrogenation zone is advanced to a second dehydrogenation zone as indicated by arrow 18 and an oxygen donor optionally can be advanced to the second dehydrogenation zone as indicated by arrow 20.

When the indene precursor to be treated in accordance with the method of the invention contains alkyl benzenes such as alkylbenzenes wherein the alkyl group contains from 9 to 16 carbon atoms, the product of the first dehydrogenation zone preferably is advanced as indicated by arrow 22 to a cyclization zone where the product is subjected to a highly acid, low temperature (for example 200°–400° C.) cyclization. The cyclized product from the cyclization zone is advanced to the second dehydrogenation zone as indicated by arrow 24.

In the second dehydrogenation zone, the product of the first dehydrogenation zone and/or the product of the cyclization zone is contacted with a dehydrogenation catalyst and oxygen if an oxygen donor has been advanced to the second dehydrogenation zone as indicated by arrow 20. Preferably, oxygen is present in the second dehydrogenation zone resulting in oxydehydrogenation of the product of the first dehydrogenation zone or the cyclization zone to indene or substituted indenes depending on the initial indene precursor. Indene formed in the second dehydrogenation zone is removed from this zone as indicated by arrow 26. If the product of the second dehydrogenation zone is an alkyl indene, the alkyl indene may be recovered if desired or advanced as indicated by arrow 28 to a dealkylation zone wherein any alkyl groups present are removed resulting in the formation of high purity indene.

Any of the various dehydrogenation and oxydehydrogenation catalysts can be used in the first and second dehydrogenation zones provided that the conditions within the zones results in the stepwise dehydrogenation of the precursor. Generally, the catalyst in the first dehydrogenation zone will be different from the catalyst utilized in the second dehydrogenation zone. The preferred group of catalysts used in the multi-stage process of the invention comprises phosphates which are salts of phosphoric acids. Any type of phosphoric acid salt can be employed such as orthophosphates, hypophosphates, metaphosphates, pyrophosphates, or other polyphosphates. Moreover, and cation can be employed, and different types of cations can be employed within a single phosphate. For example, an orthophosphate catalyst can contain one, two or three different metals depending upon the valence requirements of the phosphate. Similarly, other types of phosphates can contain one or more different metal cations as well as hydrogen.

The preferred catalysts used in the multi-stage process of the invention are characterized by the following formula $$M_a P_x O_y$$

wherein M is one or more elements selected from the group consisting of Mg, Sr, Ca, Ba, La, Ce, other rare earths, Cr, Mn, Fe, Co, Ni, Cu, Zn, Pb, Bi, Te, B, Al, Rh, Sb, As, Ge, U, Th and Ru; and $$0.1 \times \leq \Sigma a \leq 10 \times,$$

wherein $\Sigma$ a represents the sum of subscripts a of all of the metal ions and y is a number such that the valence requirements of the metal ions for oxygen are satisfied.

Specific catalysts which are useful in the process of the invention inclue $Co_{12}P_{12}O_y$, $Mg_9CrBiP_{12.5}O_y$, $Mg_9CrBiW_{0.5}P_{12.5}O_y$, $Mg_9CrBi Mo_{0.5}P_{12}O_y$, $Co_{10}Cd_2P_{12}O_y$, $Cd_{12}P_{12}O_y$, $Co_{10}SbP_{12}O_y$ and $K_{0.5}Co_9LaBiP_{12}O_y$. Additional examples of useful catalysts are included in Examples 1–6 summarized in the Table below.

The catalysts employed in the process can be used either as is or the catalysts can be supported on suitable inert supports such as alpha alumina, Alundum, silica, silicon carbide, titania, zirconia, etc. Phosphate support materials such as $BPO_4$, $TiP_2O_7$, $ZrP_2O_7$, $SbPO_4$ and $AlPO_4$ also can be employed wherein the catalyst support may exhibit some catalytic action of its own. The active catalytic component can be incorporated with a support by any known technique such as co-precipitation, impregnation, pelletizing and coating with a wet slurry or a partial dry powder. The size of the catalyst particles is not critical and can vary between wide limits. Thus, the catalyst particle size may be extremely small (e.g., microspheroidal) so that the catalyst can be employed in a fluid-bed reactor, or the catalyst can be significantly larger in particle size so that the catalyst can be employed in a fixed-bed reactor.

Although not required, it is preferred that the dehydrogenation reactions conducted in the first and second dehydrogenation zones be carried out in the presence of an oxygen donor. Elemental oxygen, $O_2$, normally is employed as an oxygen donor. In particular, air is used as a feed since it is the cheapest and most convenient source of elemental oxygen. Other compounds which will serve as oxygen donors in dehydrogenation reactions such as $SO_2$, COS, HOCl can be employed.

The amount of oxygen donor fed to the dehydrogenation zones should at least be the stoichiometric amount necessary to react with all of the hydrogen to be removed from the indene precursor feed. Lesser amounts can be fed to the reactor, but this will result in a decrease in the efficiency of the method. Preferably, the amount of oxygen donor fed to the dehyrogenation zones is at least twice and preferably from two to five times the stoichiometric amount necessary to react with all of the hydrogen withdrawn from the indene precursor.

The gaseous materials fed to the various zones also can contain a gaseous diluent. Any inert gas to the reaction and catalyst can be employed as the diluent. Preferred gaseous diluents are $N_2$, $CO_2$, $H_2O$, combustion gases, light hydrocarbon gases such as methane, etc.

Although the process of the invention can be carried out either in a fixed-bed mode or a fluid-bed mode, the fixed-bed mode is preferred. A liquid hourly space velocity of the indene precursor feed generally is from about 0.01 to 10, preferably from 0.05 to 1. The contact time for the reactants in the dehydrogenation zones generally if from 0.1 to 20 seconds, and preferably from 0.1 to 10 seconds. The reaction pressure normally is maintained at about atmospheric pressure, although lower or higher pressures can be employed if desired.

The temperature within the dehydrogenation zones must be at least 100° C. and is normally maintained between 100° and 650° C., preferably between 250° to 550° C. It has been found that the preferred reaction temperature within the dehydrogenation zones varies depending upon the particular indene precursor being processed with a temperature range of from 350°–600° C. being preferred for indane dehydrogenation and 200°–500° C. being preferred for dehydrogenation of a more saturated precursor such as tetrahydroindene.

As mentioned above, the catalysts used in the two dehydrogenation zones are different catalysts, and, generally, the catalysts used in the second dehydrogenation zone will conatin milder promoters such as La in place of stronger promoters such as Cr, or softer matrix cations such as $Co^{+2}$ in place of the harder more ionic matrix such as $Mg^{+2}$. The use of the milder promoter and softer matrix in the second dehydrogenation zone reduces the amount of indene combustion in the second dehydrogenation zone.

When alkylated indene precursors are treated in accordance with the process of this invention, the product from the second dehydrogenation zone is passed through a dealkylation zone to remove alkyl groups from the alkyl indene formed in the second dehydrogenation zone. Dealkylation is accomplished by contacting the product of the second dehydrogenation zone with a dealkylation catalyst which may be a molybdate, uranate or tungstate dealkylation catalyst alone or incorported into phosphate matrices.

The efficacy of the method of the invention is demonstrated in the following examples wherein tetrahydroindene is oxydehydrogenated to indene. Two catalyst stages using different catalysts and different temperatures are used. The catalysts have compositions as indicated in the Table below and are made by adding a concentrated solution of the respective metal nitrates to an ammonium dihydrogen phosphate solution followed by drying and calcining. For examples 1–3 in which no oxygen is added between zones, a single tubular reactor (0.5" outer diameter) is used with the top portion heated with one-fourth the wattage of the bottom section. The catalyst beds are 10 cc. each with about 5 cc. of inert material in between the catalyst beds.

For examples 4–6, the catalysts are placed in 15 cc. beds in 0.5" outer diameter stainless steel reactors. The spacers above the first bed, between the beds and at the end of the reactor are filled with alundum chips or balls. In these examples, two 18" long reactors with separate furnaces are used, and air is added through a tee between the reactors. All pressures are close to atmospheric pressure. The first reactor furnace controller is set at 425° C., and the zone 1 temperature reported in the table is the temperature near the hot spot for all runs. The zone 2 temperature is taken at the reactor skin. The reactor flows are given in the table, and the contact time for all examples is 3 seconds.

| Example[a] | Dehydrogenation Catalyst[b] | Temperature (°C.) Zone 1 | Temperature (°C.) Zone 2 | Parts Air to Zone 2 | THI Conversion | Indene Yield | Indane Yield | Indene Selectivity | Indene Indane |
|---|---|---|---|---|---|---|---|---|---|
| 1 | (1) $K_{0.5}Co_9LaBiP_{12}O_x$ (2) $K_{0.01}Co_9LaBiP_{12}O_x$ | 475 | 500 | 0 | 92% | 53.7% | 17% | 58.5% | 3.1 |
| 2 | (1) $Mg_9UBiP_{12}O_x$ (2) $Cs_{0.02}Co_9LaBiP_{12}O_x$ | 440 | 530 | 0 | 100% | 40.6% | 35% | 41% | 1.15 |
| 3 | (1) $Mg_9CrBiP_{12}O_x$ (2) $Co_9LaBiP_{12}O_x$ | 470 | 575 | 0 | 100% | 52.4% | 21% | 52.4% | 2.5 |
| 4 | (1) $Mg_{10}Cr_{0.5}BiP_{12.5}O_x$ (2) $Co_7ZrBiLaP_{12}O_x$ | 465 | 597 | 5 | 100% | 56% | 12% | 56% | 4.6 |
| 5 | (Same as Example 4) | 460 | 575 | 2.5 | 100% | 56% | 22% | 56% | 2.5 |
| 6 | (1) $Mg_{10}Cr_{0.5}BiP_{12.5}O_x$ (2) $Co_9LaBiP_{12}O_x$ | 450 | 575 | 2.5 | 100% | 54% | 24% | 54% | 2.2 |

[a]In Examples 1–3, the THI/air/$N_2$ ratio to Zone 1 is 1/9/5; LHSV overall is 0.17
In Examples 4–6, the THI/air $N_2$ ratio to Zone 1 is 1/5/4; LHSV overall is 0.2
[b]Number in parentheses refers to zone number; x is a number such that the valence requirements of the ramaining elements for oxygen are satisfied As can be seen from the results in the table, excellent yields of indene and selectivities of indene are obtaied by the method of the invention. The results in the table also indicate that generally higher yields of indene and indene/indane selectivity are obtained when the second dehydrogenation is conducted in the presence of an oxygen donor such as air.

In contrast, when an individual catalyst of the type used in examples 1–6 is placed in a single, nearly isothermal catalyst bed and tetrahydroindene mixed with air is passed through the single bed at temperatures of around 470°–530° C., the yield of indene is generally always below 50%. If the temperature of the catalyst bed is raised, the indene yield is reduced drastically by cracking tetrahydroindene. If the temperature of the single reactor is lowered, increased amounts of indane are obtained.

In summary, the method of the invention results in yields of indene which are greatly enhanced when compared to single stage, nearly isothermal processes using the same catalysts. Especially higher indene/indane ratios can be obtained while at the same time selectivity of precursor consumption can remain high. The two stage process for converting tetrahydroindene to indene generally produces at least 70% indene in the indene plus indane product while maintaining selectivity for converting tetrahydroindene at better than 75%. For a given indene yield, much lower combustion loss is sustained, and fewer losses in converting byproduct indane to indene are observed, especially when air is added to the second stage.

We claim:

1. A multi-stage catalytic dehydrogenation process for preparing indene and substituted indenes from indene precursors more saturated than indene comprising
   (a) contacting said indene precursor in a first dehydrogenation zone with a dehydrogenation catalyst at an elevated temperature to form an intermediate product,
   (b) advancing the product of the first dehydrogenation zone to a second dehydrogenation zone,
   (c) contacting said product in the second dehydrogenation zone with a second dehydrogenation catalyst at an elevated temperature, and
   (d) recovering indene or a substituted indene from said second zone.

2. The process of claim 1 wherein an oxygen donor is added to the first zone.

3. The process of claim 1 wherein an oxygen donor is added to the first and second zones.

4. The process of claim 1 wherein the temperature of the second zone is higher than the temperature of the first zone.

5. The process of claim 1 wherein the catalysts used in the two zones are different phosphate catalysts represented by the formula $$M_aP_xO_y$$

wherein M is one or more elements selected from the group consisting of Mg, Sr, Ca, Ba, La, Ce, other rare earths, Cr, Mn, Fe, Co, Ni, Cu, Zn, Pb, Bi, Te, B, Al, Rh, Sb, As, Ge, U, Th and Ru; and $$0.1x \leq \Sigma a \leq 10x,$$

wherein Σ a represents the sum of subscripts a of all of the metal ions and y is a number such that the valence requirements of the metal ions for oxygen are satisfied.

6. The process of claim 1 wherein the temperature in the zones is at least 100° C.

7. The process of claim 2 wherein the oxygen donor is $O_2$.

8. The process of claim 1 wherein the indene precursor is selected from the group consisting of indane, alkyl indanes in which the alkyl groups have from one to four carbon atoms, tetrahydroindene, alkyl tetrahydroindenes in which the alkyl groups have from one to four carbon atoms, hexahydroindene, hexahydroindane, vinyl norbornene, and alkyl benzenes in which the alkyl groups contain at least three carbon atoms.

9. The process of claim 1 wherein the indene precursor is advanced to and contacted with an isomerization catalyst in an isomerization zone prior to advancing to the first dehydrogenation zone.

10. The method of claim 9 wherein the isomerization catalyst is an acid isomerization catalyst.

11. The method of claim 9 wherein the precursor is vinyl norbornene.

12. The method of claim 1 wherein the indene precursor is an alkylated indene precursor and the alkyl indene obtained from the second dehydrogenation zone is advanced to a dealkylation zone in which the alkyl group is removed catalytically.

13. The process of claim 12 wherein the catalyst is a molybdate, uranate or tungstate dealkylation catalyst.

14. The process of claim 1 wherein the indene precursor is an alkyl benzene containing from about 9 to 16 carbon atoms and the product of the first dehydrogenation zone is advanced to and treated in a cyclization zone prior to advancement to the second dehydrogenation zone.

15. A multi-stage catalytic oxydehydrogenation process for preparing indene comprising
   (a) contacting a mixture of tetrahydroindene and a minor amount of vinyl norbornene in a first dehydrogenation zone at a temperature above about 100° C. with an oxygen source and a phosphate catalyst having the formula $$M_aP_xO_y$$

wherein M is Mg, Cr, Fe, U, Ni, Bi, or sb and $$0.1x \leq \Sigma a \leq 10x$$

wherein Σ a represents the sum of the subscripts a of all the metal ions and y is a number such that the valence requirements of the metal ions for oxygen are satisfied,
   (b) advancing the product of the first zone to a second dehydrogenation zone,
   (c) contacting said product in the second dehydrogenation zone at a temperature above about 100° C. with oxygen and a different phosphate catalyst of the formula $M_aP_xO_y$ wherein M is Mg, Co, La, Th, Bi, Sb, Pb, Ce or other rare earths and Σ a, x and y are as defined in (a) above, and
   (d) recovering indene from said second zone.

16. The process of claim 15 wherein at least one alkali metal oxide is present in either or both dehydrogenation zones.

* * * * *

The amount of oxygen donor fed to the dehydrogenation zones should at least be the stoichiometric amount necessary to react with all of the hydrogen to be removed from the indene precursor feed. Lesser amounts can be fed to the reactor, but this will result in a decrease in the efficiency of the method. Preferably, the amount of oxygen donor fed to the dehyrogenation zones is at least twice and preferably from two to five times the stoichiometric amount necessary to react with all of the hydrogen withdrawn from the indene precursor.

The gaseous materials fed to the various zones also can contain a gaseous diluent. Any inert gas to the reaction and catalyst can be employed as the diluent. Preferred gaseous diluents are $N_2$, $CO_2$, $H_2O$, combustion gases, light hydrocarbon gases such as methane, etc.

Although the process of the invention can be carried out either in a fixed-bed mode or a fluid-bed mode, the fixed-bed mode is preferred. A liquid hourly space velocity of the indene precursor feed generally is from about 0.01 to 10, preferably from 0.05 to 1. The contact time for the reactants in the dehydrogenation zones generally if from 0.1 to 20 seconds, and preferably from 0.1 to 10 seconds. The reaction pressure normally is maintained at about atmospheric pressure, although lower or higher pressures can be employed if desired.

The temperature within the dehydrogenation zones must be at least 100° C. and is normally maintained between 100° and 650° C., preferably between 250° to 550° C. It has been found that the preferred reaction temperature within the dehydrogenation zones varies depending upon the particular indene precursor being processed with a temperature range of from 350°-600° C. being preferred for indane dehydrogenation and 200°-500° C. being preferred for dehydrogenation of a more saturated precursor such as tetrahydroindene.

As mentioned above, the catalysts used in the two dehydrogenation zones are different catalysts, and, generally, the catalysts used in the second dehydrogenation zone will conatin milder promoters such as La in place of stronger promoters such as Cr, or softer matrix cations such as $Co^{+2}$ in place of the harder more ionic matrix such as $Mg^{+2}$. The use of the milder promoter and softer matrix in the second dehydrogenation zone reduces the amount of indene combustion in the second dehydrogenation zone.

When alkylated indene precursors are treated in accordance with the process of this invention, the product from the second dehydrogenation zone is passed through a dealkylation zone to remove alkyl groups from the alkyl indene formed in the second dehydrogenation zone. Dealkylation is accomplished by contacting the product of the second dehydrogenation zone with a dealkylation catalyst which may be a molybdate, uranate or tungstate dealkylation catalyst alone or incorported into phosphate matrices.

The efficacy of the method of the invention is demonstrated in the following examples wherein tetrahydroindene is oxydehydrogenated to indene. Two catalyst stages using different catalysts and different temperatures are used. The catalysts have compositions as indicated in the Table below and are made by adding a concentrated solution of the respective metal nitrates to an ammonium dihydrogen phosphate solution followed by drying and calcining. For examples 1–3 in which no oxygen is added between zones, a single tubular reactor (0.5" outer diameter) is used with the top portion heated with one-fourth the wattage of the bottom section. The catalyst beds are 10 cc. each with about 5 cc. of inert material in between the catalyst beds.

For examples 4–6, the catalysts are placed in 15 cc. beds in 0.5" outer diameter stainless steel reactors. The spacers above the first bed, between the beds and at the end of the reactor are filled with alundum chips or balls. In these examples, two 18" long reactors with separate furnaces are used, and air is added through a tee between the reactors. All pressures are close to atmospheric pressure. The first reactor furnace controller is set at 425° C., and the zone 1 temperature reported in the table is the temperature near the hot spot for all runs. The zone 2 temperature is taken at the reactor skin. The reactor flows are given in the table, and the contact time for all examples is 3 seconds.

| Example[a] | Dehydrogenation Catalyst[b] | Temperature (°C.) Zone 1 | Temperature (°C.) Zone 2 | Parts Air to Zone 2 | THI Conversion | Indene Yield | Indane Yield | Indene Selectivity | Indene Indane |
|---|---|---|---|---|---|---|---|---|---|
| 1 | (1) $K_{0.5}Co_9LaBiP_{12}O_x$ (2) $K_{0.01}Co_9LaBiP_{12}O_x$ | 475 | 500 | 0 | 92% | 53.7% | 17% | 58.5% | 3.1 |
| 2 | (1) $Mg_9UBiP_{12}O_x$ (2) $Cs_{0.02}Co_9LaBiP_{12}O_x$ | 440 | 530 | 0 | 100% | 40.6% | 35% | 41% | 1.15 |
| 3 | (1) $Mg_9CrBiP_{12}O_x$ (2) $Co_9LaBiP_{12}O_x$ | 470 | 575 | 0 | 100% | 52.4% | 21% | 52.4% | 2.5 |
| 4 | (1) $Mg_{10}Cr_{0.5}BiP_{12.5}O_x$ (2) $Co_7ZrBiLaP_{12}O_x$ | 465 | 597 | 5 | 100% | 56% | 12% | 56% | 4.6 |
| 5 | (Same as Example 4) | 460 | 575 | 2.5 | 100% | 56% | 22% | 56% | 2.5 |
| 6 | (1) $Mg_{10}Cr_{0.5}BiP_{12.5}O_x$ (2) $Co_9LaBiP_{12}O_x$ | 450 | 575 | 2.5 | 100% | 54% | 24% | 54% | 2.2 |

[a]In Examples 1–3, the THI/air/$N_2$ ratio to Zone 1 is 1/9/5; LHSV overall is 0.17
In Examples 4–6, the THI/air $N_2$ ratio to Zone 1 is 1/5/4; LHSV overall is 0.2
[b]Number in parentheses refers to zone number; x is a number such that the valence requirements of the ramaining elements for oxygen are satisfied As can be seen from the results in the table, excellent yields of indene and selectivities of indene are obtaied by the method of the invention. The results in the table also indicate that generally higher yields of indene and indene/indane selectivity are obtained when the second dehydrogenation is conducted in the presence of an oxygen donor such as air.

In contrast, when an individual catalyst of the type used in examples 1–6 is placed in a single, nearly isothermal catalyst bed and tetrahydroindene mixed with air is passed through the single bed at temperatures of around 470°–530° C., the yield of indene is generally always below 50%. If the temperature of the catalyst bed is raised, the indene yield is reduced drastically by cracking tetrahydroindene. If the temperature of the single reactor is lowered, increased amounts of indane are obtained.

In summary, the method of the invention results in yields of indene which are greatly enhanced when compared to single stage, nearly isothermal processes using the same catalysts. Especially higher indene/indane ratios can be obtained while at the same time selectivity of precursor consumption can remain high. The two stage process for converting tetrahydroindene to indene generally produces at least 70% indene in the indene plus indane product while maintaining selectivity for converting tetrahydroindene at better than 75%. For a given indene yield, much lower combustion loss is sustained, and fewer losses in converting byproduct indane to indene are observed, especially when air is added to the second stage.

We claim:

1. A multi-stage catalytic dehydrogenation process for preparing indene and substituted indenes from indene precursors more saturated than indene comprising
   (a) contacting said indene precursor in a first dehydrogenation zone with a dehydrogenation catalyst at an elevated temperature to form an intermediate product,
   (b) advancing the product of the first dehydrogenation zone to a second dehydrogenation zone,
   (c) contacting said product in the second dehydrogenation zone with a second dehydrogenation catalyst at an elevated temperature, and
   (d) recovering indene or a substituted indene from said second zone.

2. The process of claim 1 wherein an oxygen donor is added to the first zone.

3. The process of claim 1 wherein an oxygen donor is added to the first and second zones.

4. The process of claim 1 wherein the temperature of the second zone is higher than the temperature of the first zone.

5. The process of claim 1 wherein the catalysts used in the two zones are different phosphate catalysts represented by the formula $$M_aP_xO_y$$

wherein M is one or more elements selected from the group consisting of Mg, Sr, Ca, Ba, La, Ce, other rare earths, Cr, Mn, Fe, Co, Ni, Cu, Zn, Pb, Bi, Te, B, Al, Rh, Sb, As, Ge, U, Th and Ru; and $$0.1 \times \leq \Sigma a \leq 10 \times,$$

wherein $\Sigma a$ represents the sum of subscripts a of all of the metal ions and y is a number such that the valence requirements of the metal ions for oxygen are satisfied.

6. The process of claim 1 wherein the temperature in the zones is at least 100° C.

7. The process of claim 2 wherein the oxygen donor is $O_2$.

8. The process of claim 1 wherein the indene precursor is selected from the group consisting of indane, alkyl indanes in which the alkyl groups have from one to four carbon atoms, tetrahydroindene, alkyl tetrahydroindenes in which the alkyl groups have from one to four carbon atoms, hexahydroindene, hexahydroindane, vinyl norbornene, and alkyl benzenes in which the alkyl groups contain at least three carbon atoms.

9. The process of claim 1 wherein the indene precursor is advanced to and contacted with an isomerization catalyst in an isomerization zone prior to advancing to the first dehydrogenation zone.

10. The method of claim 9 wherein the isomerization catalyst is an acid isomerization catalyst.

11. The method of claim 9 wherein the precursor is vinyl norbornene.

12. The method of claim 1 wherein the indene precursor is an alkylated indene precursor and the alkyl indene obtained from the second dehydrogenation zone is advanced to a dealkylation zone in which the alkyl group is removed catalytically.

13. The process of claim 12 wherein the catalyst is a molybdate, uranate or tungstate dealkylation catalyst.

14. The process of claim 1 wherein the indene precursor is an alkyl benzene containing from about 9 to 16 carbon atoms and the product of the first dehydrogenation zone is advanced to and treated in a cyclization zone prior to advancement to the second dehydrogenation zone.

15. A multi-stage catalytic oxydehydrogenation process for preparing indene comprising
   (a) contacting a mixture of tetrahydroindene and a minor amount of vinyl norbornene in a first dehydrogenation zone at a temperature above about 100° C. with an oxygen source and a phosphate catalyst having the formula $$M_aP_xO_y$$

wherein M is Mg, Cr, Fe, U, Ni, Bi, or sb and $$0.1 \times \leq \Sigma a \leq 10 \times$$

wherein $\Sigma a$ represents the sum of the subscripts a of all the metal ions and y is a number such that the valence requirements of the metal ions for oxygen are satisfied,
   (b) advancing the product of the first zone to a second dehydrogenation zone,
   (c) contacting said product in the second dehydrogenation zone at a temperature above about 100° C. with oxygen and a different phosphate catalyst of the formula $M_aP_xO_y$ wherein M is Mg, Co, La, Th, Bi, Sb, Pb, Ce or other rare earths and $\Sigma$ a, x and y are as defined in (a) above, and
   (d) recovering indene from said second zone.

16. The process of claim 15 wherein at least one alkali metal oxide is present in either or both dehydrogenation zones.

* * * * *